United States Patent [19]

Gavlin et al.

[11] Patent Number: 5,230,778
[45] Date of Patent: Jul. 27, 1993

[54] PURIFICATION OF ISOFLURANE BY EXTRACTIVE DISTILLATION

[75] Inventors: Gilbert Gavlin, Lincolnwood; Boris Goltsin, Skokie, both of Ill.

[73] Assignees: Gavlin Associates, Lincolnwood, Ill.; Halocarbon Product Corporation, N. Augusta, S.C.

[21] Appl. No.: 878,185

[22] Filed: May 1, 1992

[51] Int. Cl.$^5$ ............................................. B01D 3/40
[52] U.S. Cl. ........................................ 203/58; 203/60; 203/62; 203/71; 568/682; 568/684
[58] Field of Search ...................... 203/58, 62, 71, 60; 568/682, 684

[56] References Cited

U.S. PATENT DOCUMENTS

| | | | |
|---|---|---|---|
| 3,113,079 | 12/1963 | Bergeron et al. | 203/58 |
| 3,658,658 | 4/1972 | Bursack et al. | 203/58 |
| 3,720,587 | 3/1973 | Croix | 203/58 |
| 5,106,460 | 4/1992 | Berg | 203/58 |

*Primary Examiner*—Virginia Manoharan
*Attorney, Agent, or Firm*—Sprung Horn Kramer & Woods

[57] ABSTRACT

A method for the separation of Isoflurane from its admixture with other compounds produced in the chlorination of 2-difluoromethoxy-1,1,1-trifluoroethane including subjecting the mixture to distillation, distilling off the Isoflurane and effecting said distillation as an extractive distillation employing an extractive solvent which retards the vapor pressure of Isoflurane.

5 Claims, No Drawings

PURIFICATION OF ISOFLURANE BY EXTRACTIVE DISTILLATION

This invention relates to the purification of 2-chloro-2-difluoromethoxy-1,1,1-trifluoroethane of the formula $CF_3CHClOCHF_2$. This material, commonly known as having the Isoflurane, is useful as an inhalation anesthetic and, as such, has to be produced essentially free of impurities.

The most important process for manufacturing Isoflurane involves the chlorination of 2-difluoromethoxy-1,1,1-trifluoroethane, $CF_3CH_2OCHF_2$, b.p. 29° C., under actinic light illumination.

This reaction generates a number of by-products in addition to Isoflurane. A typical product mixture may contain:

| Compound | b.p. (°C.) | Yield (Wt. %) |
|---|---|---|
| 1. Isoflurane $CF_3CHClOCHF_2$ | 48 | 60 |
| 2. $CF_3CH_2OCHF_2$ | 29 | 26 |
| 3. $CF_3CHClOCClF_2$ | 53 | 2 |
| 4. $CF_3CH_2OCClF_2$ | 37 | 4 |
| 5. $CF_3CCl_2OCHF_2$ | 61 | 8 |
| 6. $CF_3CCl_2OCClF_2$ | 75 | 0.2 |

Compounds 2, 4, 5 and 6 can be separated from Isoflurane by precise fractional distillation in an efficient column. Compound 3, on the other hand, co-distills and may even form a minimum boiling azeotrope with Isoflurane. U.S. Pat. No. 3,720,587 recognizes this fact and discloses a method wherein acetone, methyl ethyl ketone or tetrahydrofuran is added to the crude mixture so as to form a maximum boiling azeotrope with Isoflurane. The $CF_2CHClCClF_2$ and other by-products, being unaffected, are distilled from the azeotrope. The azeotrope is then broken by the addition of large quantities of water, allowing the distillation of Isoflurane as a water azeotrope which, after drying, yields essentially pure Isoflurane.

While this method is successful, it has several drawbacks. For example, the acetone-Isoflurane azeotrope contains about 30% acetone, requiring a larger vessel size to complete the distillation. Further, in order to break the azeotrope, at least an equal weight of water is required, thus necessitating an even larger vessel. The water left behind after the removal of Isoflurane contains residual organic materials together with azeotropic solvent and has to be treated before disposal. Finally, the Isoflurane obtained is wet and has to be dried, thus requiring another operational step.

There is a need, therefore, for an improved purification method to produce essentially pure Isoflurane, and that is the object of the present invention.

It has now been found that Isoflurane produced by the chlorination of $CF_3CH_2OCHF_2$ may be obtained essentially pure by an extractive distillation process in a multi-stage column.

Extractive distillation is a method of separating close boiling compounds by carrying out a fractional distillation in a multi-stage column in the presence of an added solvent or solvent mixture. The solvent is added near the top of the column at the boiling temperature at that location which is close to the boiling temperature of the original mixture. The key to the process is to use a solvent that has a selective effect on the principal component of the original mixture, and will alter its relative volatility, i.e. retard its vapor pressure, thereby making possible an efficient separation which would not at all occur in the absence of such solvent.

The normal method of conducting an extractive distillation is in a continuous column with uniform continuous feeds near the top of the column. At the bottom, the contents of the reboiler are continuously removed. This should comprise mainly extraction solvent and the principal component of the original mixture. No original components difficult to separate by distillation should be present. Usually the selective solvent is isolated in a separate rectification column.

It is essential to practical extractive distillation that the selective solvent not form an azeotrope with any component of the mixture to be separated. For this reason, it is preferable for the solvent to boil a minimum of 25° C. higher. This difference will also simplify recovery of the solvent for reuse.

There has been discovered the following series of solvents with which to separate Isoflurane from its synthesis by-products in an extractive distillation process:

| Solvent | b.p. (°C.) |
|---|---|
| dimethylformamide | 145 |
| dimethylacetamide | 165 |
| N-methylpyrrolidone | 205 |
| acetone | 57 |

Each of these solvents alters the volatility of Isoflurane relative to the other organic components of the original mixture, thus making it possible to isolate Isoflurane dry and pure.

EXAMPLE 1

A batch extractive fractional distillation was carried out in an Oldershaw-type column containing twenty-four glass sieve trays with downcomers, and with a feed line located at Tray 15. Feed rate was maintained with a precision piston-type metering pump; feed temperature was controlled with an electric tube heater. A 500 g feed charge, having the following composition, was placed in a three liter still pot:

| | Charge | Wt. % | b.p. (°C.) |
|---|---|---|---|
| Isoflurane | $CH_3CH_2OCHF_2$ | 0.1 | 29 |
| | $CF_3CH_2OCClF_2$ | 0.3 | 37 |
| | $CF_3CHClOCHF_2$ | 87.9 | 48 |
| | $CF_3CHClOCClF_2$ | 1.3 | 53 |
| | $CF_3CCl_2OCHF_2$ | 10.5 | 61 |
| | $CF_3CCl_2OCClF_2$ | 0.1 | 75 |

Hereafter, each compound is designated by its boiling point. All analytical data have been obtained by gas chromatography.

The charge was brought to total reflux and maintained there for forty-five minutes at which time the reflux, b.p. 46° C., had the following composition:

| Reflux Composition | |
|---|---|
| Cpd | Wt. % |
| 29 | 1.4 |
| 37 | 3.1 |
| 48 | 92.8 |
| 53 | 1.9 |
| 61 | 0.8 |

-continued

| Reflux Composition | |
| --- | --- |
| Cpd | Wt. % |
| 75 | 0.1 |

Feed of the extractive agent, dimethylformamide, DMF, was initiated at 20 ml/min, 56° C., on Tray 15. When the overhead temperature rose to 55° C. indicating loss of 48, distillate take-off was started and continued until the 48 content of the overhead reached 99%. The bulk of this forerun had the following composition:

| Forerun | |
| --- | --- |
| Cpd | Wt. % |
| 29 | 0.7 |
| 37 | 1.6 |
| 48 | 15.0 |
| 53 | 10.2 |
| 61 | 71.6 |
| 75 | 0.3 |
| | 99.4 |

Overhead take-off was then switched to final product for which the composition was:

| Extractive Distillation Final Product | |
| --- | --- |
| Cpd | Wt. % |
| 29 | 0 |
| 37 | 0 |
| 48 | 99.1 |
| 53 | Trace |
| 61 | 0.9 |
| 75 | 0 |

Isoflurane, Cpd. 48, could be separated from 61 by normal fractional distillation.

EXAMPLE 2

The equipment of Example 1 was modified by the addition of a second feed system at the top of the column, Tray 24, and a product removal system from the stillpot. This enabled operation of the entire assembly as a continuous distillation facility. An extractive distillation run was initiated by refluxing a small charge of 200–400 g of dimethylformamide, DMF, in the stillpot. Feed I on Tray 15 was crude Isoflurane, Feed II on Tray 24 was good quality DMF. Typically, crude Isoflurane had the following composition:

| Crude Isoflurane | |
| --- | --- |
| Cpd | Wt. % |
| 29 | 5.8 |
| 37 | 1.9 |
| 48 | 86.8 |
| 53 | 0.9 |
| 61 | 4.6 |
| 75 | — |

Feeds I and II were initiated at the same time at 6 ml/min and 20 ml/min respectively, at the projected temperature within the column at steady state. In the usual run, two liters of crude Isoflurane was fed into the column. A typical distillate had the following composition:

| Extractive Distillation A Distillate Composition | |
| --- | --- |
| Cpd | Wt. % |
| 29 | 36.6 |
| 37 | 13.8 |
| 48 | 3.4 |
| 53 | 7.6 |
| 61 | 35.8 |
| 75 | — |
| DMF | 2.8 |
| | 100.0 |

The final product from Extractive distillation A was obtained by stripping the DMF solution obtained from the stillpot, through a fractionating column:

| Extractive Distillation A Final Product Composition | |
| --- | --- |
| Cpd | Wt. % |
| 29 | 0.0065 |
| 37 | 0.0059 |
| 48 | 99.6 |
| 53 | 0.0013 |
| 61 | 0.0183 |
| 75 | — |
| DMF | 0.3 |

By repeating the extractive distillation with this product and carefully fractionating, Isoflurane could be obtained in a purity greater than 99.9990.

It will be understood that the specification and examples are illustrative but not limitative of the present invention and that other embodiments within the spirit and scope of the invention will suggest themselves to those skilled in the art.

What is claimed is:

1. In a separation of Isoflurane from its admixture with other compounds produced in the chlorination of 2-difluoromethoxy-1,1,1-trifluoroethane by subjecting the mixture to distillation and distilling off the Isoflurane, the improvement which comprises effecting said distillation as an extractive distillation employing an extractive solvent which retards the vapor pressure of Isoflurane, said solvent selected from a group consisting of dimethylformamide, dimethylacetamide, N-methylpyrrolidone and acetone.

2. The process according to claim 1, wherein the extractive solvent is dimethylacetamide.

3. The process according to claim 1, wherein the extractive solvent is dimethylformamide.

4. The process according to claim 3, wherein the product of the extractive distillation is subjected to a further distillation to recover Isoflurane.

5. The process according to claim 1, wherein the extractive solvent is acetone.

* * * * *